US011236032B2

(12) United States Patent
Dennis-Smither et al.

(10) Patent No.: US 11,236,032 B2
(45) Date of Patent: Feb. 1, 2022

(54) PROCESS FOR DEHYDRATING METHANOL TO DIMETHYL ETHER

(71) Applicants: BP P.L.C., London (GB); BP (CHINA) HOLDINGS LTD, Shanghai (CN)

(72) Inventors: Benjamin James Dennis-Smither, Hull (GB); John Glenn Sunley, Hull (GB); Zhiqiang Yang, Liaoning (CN)

(73) Assignee: BP P.L.C., London (GB)

( * ) Notice: Subject to any disclaimer, the term of this patent is extended or adjusted under 35 U.S.C. 154(b) by 0 days.

(21) Appl. No.: 16/641,642

(22) PCT Filed: Aug. 24, 2018

(86) PCT No.: PCT/CN2018/102057
§ 371 (c)(1),
(2) Date: Feb. 24, 2020

(87) PCT Pub. No.: WO2019/037764
PCT Pub. Date: Feb. 28, 2019

(65) Prior Publication Data
US 2021/0163390 A1    Jun. 3, 2021

(30) Foreign Application Priority Data

Aug. 24, 2017  (WO) ............... PCT/CN2017/098839

(51) Int. Cl.
| C07C 41/09 | (2006.01) |
| B01J 29/40 | (2006.01) |
| B01J 29/70 | (2006.01) |
| B01J 29/18 | (2006.01) |
| B01J 29/08 | (2006.01) |
| B01J 23/30 | (2006.01) |
| C07C 43/04 | (2006.01) |

(52) U.S. Cl.
CPC .............. *C07C 41/09* (2013.01); *B01J 23/30* (2013.01); *B01J 29/08* (2013.01); *B01J 29/18* (2013.01); *B01J 29/40* (2013.01); *B01J 29/7007* (2013.01); *B01J 29/7015* (2013.01); *B01J 29/7042* (2013.01); *B01J 29/7046* (2013.01); *C07C 43/043* (2013.01)

(58) Field of Classification Search
CPC ....... C07C 41/09; B01J 29/40; B01J 2229/34; B01J 2229/42; B01J 29/65; B01J 29/70; B01J 29/7015; B01J 29/7007; B01J 29/7046; B01J 29/7042; B01J 29/18; B01J 23/30; B01J 29/85; B01J 29/08
See application file for complete search history.

(56) References Cited

U.S. PATENT DOCUMENTS

| 4,560,807 A | 12/1985 | Nobuyuki et al. |
| 2012/0220804 A1 | 8/2012 | Mitschke et al. |
| 2017/0081267 A1 | 3/2017 | Daniel et al. |
| 2017/0096382 A1 | 4/2017 | Beckers et al. |

FOREIGN PATENT DOCUMENTS

| AU | 2008353375 A1 * | 10/2009 | ............. C07C 43/04 |
| CN | 1810752 | 8/2006 | |
| CN | 1820849 | 8/2006 | |
| CN | 101486629 | 7/2009 | |
| CN | 104341279 | 2/2015 | |
| CN | 105669452 | 6/2016 | |
| EP | 1396483 | 10/2004 | |
| WO | 2004074228 | 9/2004 | |
| WO | 2011027105 | 3/2011 | |
| WO | 2013124404 | 8/2013 | |
| WO | 2013124423 | 8/2013 | |
| WO | 2014096254 | 6/2014 | |
| WO | 2014125038 | 8/2014 | |
| WO | 2015121411 | 8/2015 | |
| WO | 2015193179 | 12/2015 | |
| WO | 2015193182 | 12/2015 | |
| WO | 2015193183 | 12/2015 | |
| WO | 2015193185 | 12/2015 | |
| WO | 2015193186 | 12/2015 | |
| WO | 2015193188 | 12/2015 | |

OTHER PUBLICATIONS

Foster, M.D., et al., Microporous and Mesoporous Materials, vol. 90, pp. 32-38, 2006.
The International Search Report with Written Opinion for PCT/CN2018/102072 dated Oct. 26, 20187, p. 1-11.
The International Search Report with Written Opinion for PCT/CN2017/098861 dated May 23, 2018, p. 1-11.
The International Search Report with Written Opinion for PCT/CN2018/102137 dated Nov. 28, 2018, p. 1-9.
The International Search Report with Written Opinion for PCT/CN2017/098885 dated May 30, 2018, p. 1-10.
The International Search Report with Written Opinion for PCT/CN2018/102057 dated Nov. 9, 2018, p. 1-11.
The International Search Report with Written Opinion for PCT/CN2017/098839 dated May 22, 2018, p. 1-11.
The International Search Report with Written Opinion for PCT/CN2018/101954 dated Nov. 19, 2018, p. 1-11.
The International Search Report with Written Opinion for PCT/CN2017/098892 dated May 22, 2018, p. 10.

* cited by examiner

*Primary Examiner* — Rosalynd A Keys
(74) *Attorney, Agent, or Firm* — McDonnell Boehnen Hulbert & Berghoff LLP

(57) ABSTRACT

A process for dehydrating methanol to dimethyl ether using a Brønsted acid catalyst which is a 1-dimensional or a 3-dimensional aluminosilicate zeolite or a heteropolyacid, and a promoter of Formula I $C_nH_{(2n+1)}CO_2CH_3$ wherein n=1 to 11 or Formula II $C_mH_{2m}(CO_2CH_3)_2$ wherein m=2 to 7 and the molar ratio of promoter to methanol is maintained at less than 1.

18 Claims, No Drawings

PROCESS FOR DEHYDRATING METHANOL TO DIMETHYL ETHER

This application is a national stage application under 35 U.S.C. § 371 of International Application No. PCT/CN2018/102057, filed Aug. 24, 2018, which claims priority to International Application No. PCT/CN2017/098839, filed Aug. 24, 2017, the disclosures of which are explicitly incorporated by reference herein.

This invention relates in general to a dehydration process and in particular to a process for the dehydration of methanol in the presence of a solid Brønsted acid catalyst and a promoter compound.

Industrial processes for the dehydration of methanol to dimethyl ether using non-zeolitic catalysts such as alumina are known. Such processes employing alumina catalysts are described, for example in EP-A-1396483. Although these alumina catalysts are solid acid catalysts they are not Brønsted acid catalysts.

Processes for the dehydration of alcohols such as methanol employing zeolite catalysts are known and described, for example in WO 2004/074228.

WO 2004/074228 describes a process for preparing dimethyl ether in high yield by employing a dual-catalyst system. Methanol is initially dehydrated over a hydrophilic solid acid catalyst such as gamma-alumina; unreacted methanol is then dehydrated over a second solid acid catalyst, a hydrophobic zeolite such as ZSM-5.

EP-A-1396483 and WO 2004/074228 exemplify the use of high reaction temperatures, typically 250° C. and higher. Whilst the use of such high reaction temperatures may be desirable to achieve acceptable reaction rates, a disadvantage is that at temperatures, typically in excess of 250° C., hydrocarbons are co-produced with the dimethyl ether product and this typically leads to a reduction in catalytic performance.

WO 2011/027105 describes a process for the simultaneous dehydration of methanol and hydrolysis of methyl acetate. The process can be conducted at reaction temperatures below 250° C. by employing a zeolite having a 2-dimensional framework structure comprising at least one channel having a 10-membered ring. Examples of such zeolites are zeolites of framework type FER typified by ferrierite and HEU typified by clinoptilolite.

Processes for the co-production of acetic acid and dimethyl ether by the dehydration of methanol and hydrolysis of methyl acetate in the presence of zeolites having a 2-dimensional framework structure are also described, for example in WO 2013/124404 and WO 2013/124423.

Processes in which methanol-containing streams are dehydrated over solid acid catalysts such as heteropolyacids, gamma-aluminas or zeolites are described, for example in WO 2015/193186 and WO 2015/193188.

Applicant has now found that compounds which are (i) alkyl carboxylate esters of Formula I $C_nH_{(2n+1)}CO_2CH_3$ or (ii) di-ester compounds of Formula II $C_mH_{2m}(CO_2CH_3)_2$ in which Formulae n=1 to 11 and m=2 to 7, have a beneficial effect on the rate of dehydration of methanol reactions carried out in the presence of solid Brønsted acid catalysts which are aluminosilicate zeolites which have a 1-dimensional or 3-dimensional framework structure or heteropolyacids.

Accordingly, the present invention provides a process for dehydrating methanol to dimethyl ether product in the presence of a catalyst and promoter, wherein the catalyst is at least one solid Brønsted acid catalyst selected from (a) aluminosilicate zeolites which have a 1-dimensional or a 3-dimensional framework structure or (b) heteropolyacids, and the promoter is:

(i) at least one an alkyl carboxylate ester, $C_nH_{(2n+1)}CO_2CH_3$ (Formula I); or (ii) at least one di-ester compound, $C_mH_{2m}(CO_2CH_3)_2$ (Formula II), wherein in Formula I, n=1 to 11; and in Formula II, m=2 to 7 and wherein and the molar ratio of promoter to methanol is maintained at less than 1.

Advantageously, the promoters of the present invention allow productivity to dimethyl ether product to be improved in dehydration reactions of methanol which are carried out in the presence of solid Brønsted acid catalysts which are aluminosilicate zeolites or heteropolyacids and salts thereof.

Also, according to the present invention there is provided a method of improving the productivity to dimethyl ether product in a process for dehydrating methanol in the presence of a catalyst and a promoter, wherein the catalyst is at least one solid Brønsted acid catalyst selected from (a) aluminosilicate zeolites which have a 1-dimensional or a 3-dimensional framework structure or (b) heteropolyacids, and the promoter is:

(i) at least one an alkyl carboxylate ester, $C_nH_{(2n+1)}CO_2CH_3$ (Formula I); or (ii) at least one di-ester compound, $C_mH_{2m}(CO_2CH_3)_2$ (Formula II), wherein in Formula I, n=1 to 11; and in Formula II, m=2 to 7 and wherein and the molar ratio of promoter to methanol is maintained at less than 1.

Yet further according to the present invention there is provided the use of a promoter in a process for the catalytic dehydration of methanol to dimethyl ether to improve productivity to dimethyl ether product wherein the catalyst is at least one solid Brønsted acid catalyst selected from (a) aluminosilicate zeolites which have a 1-dimensional or a 3-dimensional framework structure or (b) heteropolyacids, and the promoter is:

(i) at least one an alkyl carboxylate ester, $C_nH_{(2n+1)}CO_2CH_3$ (Formula I); or (ii) at least one di-ester compound, $C_mH_{2m}(CO_2CH_3)_2$ (Formula II), wherein in Formula I, n=1 to 11; and in Formula II, m=2 to 7 and wherein and the molar ratio of promoter to methanol is maintained at less than 1.

A further aspect of the present invention provides a process for dehydrating methanol to dimethyl ether product in the presence of a catalyst, wherein the catalyst is at least one solid Brønsted acid catalyst selected from (a) aluminosilicate zeolites which have a 1-dimensional or a 3-dimensional framework structure or (b) heteropolyacids, and wherein prior to using the catalyst in the dehydration process, the catalyst has been impregnated with a promoter selected from:

(i) at least one an alkyl carboxylate ester, $C_nH_{(2n+1)}CO_2CH_3$ (Formula I); or (ii) at least one di-ester compound, $C_mH_{2m}(CO_2CH_3)_2$ (Formula II), wherein in Formula I, n=1 to 11; and in Formula II, m=2 to 7.

The catalytic dehydration reaction of methanol can be represented by the following equation: 2 methanol ⇌ dimethyl ether+water.

In the present invention, the dehydration process is carried out in the presence of at least one solid Brønsted acid catalyst selected from aluminosilicate zeolites and heteropolyacids and salts thereof. As would be understood by the skilled person in the art, by 'Brønsted acid catalyst' is meant an acid catalyst which has the ability to donate an acidic proton to facilitate a chemical reaction.

In some or all embodiments of the present invention, the Brønsted acid catalyst is selected from aluminosilicate zeolites.

Aluminosilicate zeolites are crystalline microporous materials which have framework structures constructed from tetrahedra of $SiO_4$ and $AlO_4$ that share vertices. Such tetrahedral species are generally referred to as $TO_4$ species wherein the T atom is silicon or aluminium. Aluminium 'T' atoms can be partially or wholly replaced by one or more gallium, boron or iron atoms. For the purposes of the present invention, such gallium, boron or iron modified zeolites are considered to fall within the definition of the term 'aluminosilicate zeolites'.

Silicoaluminophosphate structures containing $PO_4$ tetrahedra are not considered to be aluminosilicate materials and consequently, such silicoaluminophosphates, for example SAPO-type materials, are not within the scope of the present invention.

A zeolite framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC.

A description of zeolites, their framework codes, structure, dimensionality, properties and methods of synthesis can be found in The *Atlas of Zeolite Framework Types* (C. Baerlocher, W. M. Meier, D. H. Olson, $5^{th}$ Ed. Elsevier, Amsterdam, 2001) in conjunction with the web-based version (http://www.iza-structure.org/databases/).

Zeolite crystals contain pore or channel systems of molecular dimensions with fixed geometry and size and can be classified according to the number of channels running in different directions within the zeolite framework structure. A zeolite is described as 1-dimensional, 2-dimensional or 3-dimensional if the zeolite has one, two or three channels in different directions, respectively. Zeolites for use in the present invention possess a 1-dimensional or a 3-dimensional framework structure.

In some or all embodiments of the present invention the Brønsted acid catalyst is a zeolite which zeolite has a 1-dimensional framework structure and, suitably is a zeolite selected from framework types MOR, TON and MTT. Examples of zeolites having framework type MOR include mordenite. Examples of zeolites having framework type TON include ZSM-22 and theta-1. Examples of zeolites having framework type MTT include ZSM-23.

In some or all embodiments of the present invention the Brønsted acid catalyst is a zeolite which zeolite has a 3-dimensional framework structure and, suitably is a zeolite selected from framework types MFI, FAU, CHA and BEA. Examples of zeolites of framework type MFI include ZSM-5. Examples of zeolites of framework type FAU include zeolite Y and zeolite X. Examples of zeolites of framework type CHA include chabazite, SSZ-13 and SSZ-62. Examples of zeolites of framework type BEA include zeolite beta and SSZ-26.

Zeolites may also be classified according to the size of their pores. Zeolites with pore openings limited by 8 T atoms in tetrahedral co-ordination are defined as "small pore zeolites" (8-membered rings). Zeolites with pore openings limited by 10 T atoms in tetrahedral co-ordination are defined as "medium pore zeolites" (10-membered rings). Zeolites with pore openings limited by 12 T atoms in tetrahedral co-ordination are defined as "large pore zeolites" (12-membered rings).

The extent to which the dehydration reaction is promoted may vary depending on factors such as the structure of the zeolite and nature of the promoter employed in the reaction. Desirably, to promote increased productivity to dimethyl ether, the channels of a zeolite must be of a size such that a promoter is able to diffuse freely through the zeolite channels.

In some or all embodiments of the present invention, the Brønsted acid catalyst is a zeolite which zeolite is a medium or large pore zeolite.

In some or all embodiments of the present invention, the Brønsted acid catalyst is a zeolite which zeolite is a large pore zeolite. Examples of large pore zeolites include those of framework types, MOR, FAU, BEA, MTT, GME, IWW, MAZ, LTL and OFF and ITQ-type zeolites such as ITQ-7 and ITQ-26.

In some or all embodiments of the present invention, the Brønsted acid catalyst is a zeolite which zeolite is a medium pore zeolite. Examples of medium pore zeolites include those of the framework types MFI and TON and also ITQ-type zeolites, such as ITQ-13 and ITQ-34

In some or all embodiments of the present invention, the zeolite is selected from zeolites of framework type MOR, MFI or BEA, such as mordenite, ZSM-5 and zeolite beta respectively.

Typically, zeolites are synthesised from synthesis mixtures comprising a silica source, an alumina source, alkali metal hydroxide and water in desired proportions. The synthesis mixture is maintained, with or without agitation, under temperature, pressure and time conditions sufficient to form a crystalline aluminosilicate zeolite. The resulting zeolite contains alkali metal as a cation. Such cations may be replaced by known ion-exchange techniques. For example, the zeolite may be contacted with aqueous solutions of ammonium salts to substitute ammonium ions for the alkali metal cations. Ammonium-form zeolites are also available commercially.

Whilst zeolites in their ammonium-form can be catalytically active, for use in the present invention it is preferred to utilise a zeolite in its hydrogen-form (H-form). H-form zeolites are commercially available. Alternatively, an ammonium-form zeolite can be converted to the H-form by known techniques, for example by calcining the ammonium-form zeolite, in air or inert gas, at high temperature, for example at a temperature of 500° C. or higher.

In some or all embodiments of the present invention, the Brønsted acid catalyst is a zeolite which zeolite is a hydrogen-form (H-form) zeolite.

For use in the present invention, a zeolite may be composited with at least one binder material. The binder material may be a refractory inorganic oxide, such as silicas, aluminas, alumina-silicates, magnesium silicates, magnesium aluminium silicates, titanias and zirconias.

For use in the present invention the relative proportions of zeolite and binder material in the composite may vary widely. Suitably, the binder material can be present in an amount of from 10% to 90% by weight of the composite.

For use in the present invention, the silica to alumina molar ratio of a zeolite may vary widely but suitably is in the range 10 to 300, for example in the range 20 to 280, such as in the range 20 to 100.

The promoter compounds of the present invention have also been found to be beneficial in promoting methanol dehydration reactions which are catalysed by heteropolyacid catalysts.

The term "heteropolyacid" as used herein and throughout this specification is meant to include the free acids and salts thereof. Heteropolyacids for use in the present invention may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions.

In some or all embodiments of the present invention, the Brønsted acid catalyst is a heteropolyacid which heteropolyacid is selected from silicotungstic acids, phosphotungstic acids and 12-tungstophosphoric acid ($H_3[PW_{12}O_{40}].xH_2O$); 12-molybdophosphoric acid ($H_3[PMo_{12}O_{40}].xH_2O$); 12-tungstosilicic acid ($H_4[SiW_{12}O_{40}].xH_2O$); 12-molybdosilicic acid ($H_4[SiMo_{12}O_{40}].xH_2O$) and salts thereof, for example ammonium salts of heteropolyacids, such as ammonium salts of a phosphotungstic acid or a silicotungstic acid.

In some or all embodiments of the present invention the Brønsted acid catalyst is a heteropolyacid which heteropolyacid is a silicotungstic acid.

Heteropolyacids for use in the present invention may be supported on any suitable support such as refractory inorganic oxides, for example silicas, aluminas and silica-aluminas.

Promoter compounds for use in the present invention are (i) at least one alkyl carboxylate ester of Formula I, $C_nH_{(2n+1)}CO_2CH_3$ wherein n=1 to 11 or (ii) at least one di-ester compound of Formula II, $C_mH_{2m}(CO_2CH_3)_2$ wherein m=2 to 7.

Mixtures of esters of Formula I and di-esters of Formula II may also be used in the present invention.

In some or all embodiments of the present invention, the alkyl carboxylate ester of Formula I is an alkyl carboxylate ester wherein n=1 to 9, such as n=2 to 7, for example wherein n=3 to 7.

In the present invention, an alkyl carboxylate ester of Formula I may be a straight alkyl chain carboxylate ester or a branched alkyl chain carboxylate ester.

In some or all embodiments of the present invention, the alkyl carboxylate ester of Formula I is a straight alkyl chain carboxylate ester wherein n=1 to 9.

In some or all embodiments of the present invention, the alkyl carboxylate ester of Formula I is a straight alkyl chain carboxylate ester wherein n=2 to 7.

In some or all embodiments of the present invention, the alkyl carboxylate ester of Formula I is a straight alkyl chain carboxylate ester wherein n=3 to 7.

Specific non-limiting examples of straight alkyl chain carboxylate esters of Formula I suitable for use in the present invention are methyl acetate, methyl propionate, methyl n-butyrate, methyl n-pentanoate, methyl n-hexanoate, methyl n-heptanoate and methyl n-octanoate.

In some or all embodiments of the present invention, the di-ester compound of Formula II is a di-ester wherein m=2 to 4.

In some or all embodiments of the present invention, the di-ester compound of Formula II is selected from at least one of dimethyl succinate, dimethyl glutarate and dimethyl adipate.

In the present invention, a promoter may be added as a component of the feed to the dehydration process. Alternatively and/or additionally, a promoter may be generated in-situ by the addition to the process of any compound (a precursor compound) from which an alkyl carboxylate ester of Formula I or di-ester compound of Formula II can be generated in-situ.

Precursor compounds which can be used for the in-situ generation of the alkyl carboxylate ester promoter compounds of Formula I, $C_nH_{(2n+1)}CO_2CH_3$, wherein n=1 to 11, include compounds of formula $C_pH_{(2p+1)}CO_2X$ wherein the value of p corresponds to that of n in Formula I and X is selected from hydrogen, a $C_2$ or higher alkyl group, halogen, such as chlorine, and a —C(=O)—R' group wherein $R^1$ is hydrogen or an alkyl group.

Precursor compounds which can be used for the in-situ generation of the di-ester promoter compounds of Formula II, $C_mH_{2m}(CO_2CH_3)_2$ wherein m=2 to 7, include compounds of formula $C_dH_{(2d)}(CO_2X)_2$ wherein the value of d corresponds to that of m in Formula II and each X may be the same or different and is selected from hydrogen, a $C_2$ or higher alkyl group, halogen, such as chlorine, and a —C(=O)—R' group wherein $R^1$ is hydrogen or an alkyl group.

In the present invention the molar ratio of promoter to methanol is maintained throughout the dehydration reaction at less than 1. In some or all embodiments of the present invention the molar ratio of promoter to methanol is maintained in the range 0.000001:1 to less than 0.5:1, preferably in the range of 0.00005:1 to less than 0.5:1. In some or all embodiments of the present invention, the molar ratio of promoter to methanol is maintained in the range of 0.00001:1 to less than 0.5:1, for example 0.00005:1 to 0.2:1, such as 0.0001:1 to 0.2:1. In some or all embodiments of the present invention, the molar ratio of promoter to methanol is maintained in the range of 0.01:1 to less than 0.5:1, for example 0.01:1 to 0.2:1, such as 0.02:1 to 0.2:1.

Suitably, in the present invention the total amount of promoter relative to the total amount of methanol is maintained throughout the dehydration reaction in an amount of at least 1 ppm. In some or all embodiments of the present invention, the total amount of promoter relative to the total amount of methanol is maintained throughout the dehydration reaction in an amount of at least 0.001 mol %, for example in an amount of 0.001 mol % to less than 50 mol %, such as 0.001 mol % to 20 mol %, for instance 0.005 mol % to 20 mol %. In some or all embodiments of the present invention, the total amount of promoter relative to the total amount of methanol is maintained throughout the dehydration reaction in an amount of at least 0.01 mol %, for example in an amount of 0.01 mol % to less than 50 mol %, such as 0.01 mol % to 20 mol %, for instance 0.05 to 20 mol %. In some or all embodiments of the present invention, the total amount of promoter relative to the total amount of methanol is maintained throughout the dehydration reaction in an amount of at least 1 mol %, for example in an amount of 1 mol % to less than 50 mol %, such as 1 mol % to 20 mol %, for instance 2 to 20 mol %.

In some or all embodiments of the present invention, the promoter is an alkyl carboxylate ester of Formula I, suitably an alkyl carboxylate ester of Formula I which is a straight alkyl chain carboxylate ester wherein n=1 to 9, preferably n=2 to 7, for example wherein n=3 to 7, and suitably the concentration of promoter relative to methanol is maintained in an amount of 0.01 to 20 mol %, for example 2 to 20 mol %, and the Brønsted acid catalyst is a zeolite which zeolite is a large pore zeolite, suitably selected from zeolites of framework type MOR or BEA, such as mordenite, and zeolite beta respectively or a medium pore zeolite, suitably of framework type MFI, for example ZSM-5. In these embodiments, the zeolite may have a silica to alumina molar ratio in the range 10 to 300, for example in the range 20 to 280, suitably in the range 20 to 100.

In some or all embodiments of the present invention, the promoter is di-ester compound of Formula II is selected from at least one of dimethyl succinate, dimethyl glutarate and dimethyl adipate and suitably the concentration of promoter relative to methanol is maintained in an amount of 0.01 to 20 mol %, for example 2 to 20 mol %, and the Brønsted acid catalyst is a zeolite which is a large pore zeolite, suitably selected from zeolites of framework type MOR or BEA, such as mordenite, and zeolite beta respectively or a medium pore zeolite, suitably of framework type MFI, for example ZSM-5. In these embodiments, the zeolite may have a silica to alumina molar ratio in the range 20 to 280, suitably in the range 20 to 100.

In some or all embodiments of the present invention, the promoter is an alkyl carboxylate ester of Formula I, suitably an alkyl carboxylate ester of Formula I which is a straight alkyl chain carboxylate ester wherein 1 to 9, preferably n=2 to 7, for example wherein n=3 to 7 and suitably the concentration of promoter relative to methanol is maintained in an amount of 0.01 to 20 mol %, for example 2 to 20 mol %, and the Brønsted acid catalyst is a heteropolyacid which heteropolyacid is suitably a silicotungstic acid.

In some or all embodiments of the present invention, the solid Brønsted acid catalyst may be impregnated with the promoter prior to being used in the dehydration process. The method of impregnation is not limited and any technique known in the art may be used, for example, incipient wetness technique or excess solution technique. The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation. The promoter may be used as the impregnation solution directly, or a dilute solution of the promoter may be used. When a dilute solution of promoter is used, the solvent for the impregnation solution may suitably be an aqueous solution, an organic solution, or a mixture of aqueous and organic solvent(s), depending upon the solubility of the promoter being used; non-limiting examples of suitable solvents include water, alcohols, for example methanol, ethers, and mixtures thereof, such as aqueous alcoholic solutions, for example an aqueous methanol solution.

Suitably, in the present invention, the dehydration process may be carried out as a standalone process. In such cases the dehydration reaction is not, for example carried out as part of a co-production process, such as co-production processes for the production of acetic acid and dimethyl ether by dehydration of methanol and hydrolysis of a methyl acetate co-feed. Thus, suitably, in the present invention, the feed components to the process are methanol and at least one compound which is a promoter compound of Formula I or Formula II or a precursor compound thereof.

However, typically, the product stream of the methanol dehydration reaction will comprise dimethyl ether, water, unconverted methanol and one or more compounds selected from promoter compounds of Formula I or Formula II and precursor compounds of the promoter compounds of Formula I or Formula II. Thus, in some or all embodiments of the present invention, one or more components of the product stream of the dehydration process are recycled as feed to the process. In such instances one or both of dimethyl ether and water are additional feed components to the dehydration process.

Thus, in some or all embodiments of the present invention the feed components to the dehydration process are methanol, at least one promoter selected from Formula I or Formula II and one or both of dimethyl ether and water.

In instances where it is desired to generate the promoter in situ in the dehydration process the feed components to the process may be methanol and at least one precursor compound of the promoters of Formula or Formula II.

Thus, in some or all embodiments of the present invention the feed components to the dehydration process are methanol, one or both of (i) at least one promoter compound of Formula I or Formula II and (ii) at least one precursor compound of a promoter compound of Formula I or Formula II; and one or both of dimethyl ether and water.

The feed components to the process may be supplied to the process in one or more feed streams.

Preferably, methyl acetate is not a component of the feed to the process.

The dehydration process is carried out as a heterogeneous process, either as a vapour phase heterogeneous process or as a liquid phase heterogeneous process.

The type of reactor used for the dehydration process is not limited, and it may be suitably carried out in any type of reactor within which a vapour phase heterogeneous process or a liquid phase heterogeneous process may be performed. Non-limiting types of reactors with which the dehydration reaction may be performed include tank reactors, multi-tubular reactors, plug-flow reactors, loop reactors, fluidized bed reactors, and reactive distillation columns.

The dehydration process may be carried out at a temperature of from 100 to 300° C. In some or all embodiments of the present invention, the dehydration process is carried out at a temperature of from 140 to 250° C., for example from 150 to 250° C.

Suitably, the dehydration process may be carried out at atmospheric pressure or at elevated pressure.

In some or all embodiments of the present invention, the dehydration process is carried out at a total pressure of atmospheric pressure to 3000 kPa. Where the process is conducted in the liquid phase, higher total pressures, such as 4000 kPa to 10,000 kPa, may be required to maintain the dimethyl ether product in solution.

In some or all embodiments of the present invention, the dehydration process is carried out as a heterogeneous vapour phase process at a total pressure of atmospheric pressure to 3000 kPa. In these embodiments, the temperature may be from 100 to 300° C., such as from 140 to 250° C., for example from 150 to 250° C.

For vapour phase processes, the process may be carried out at a total gas hourly space velocity (GHSV) in the range 500 to 40,000 h$^{-1}$.

For liquid phase processes, the process may be carried out at a total liquid hourly space velocity (LHSV) in the range 0.2 to 20 h$^{-1}$.

The dehydration process may be carried out using one or more beds of zeolite catalyst, suitably selected from fixed bed, fluidised bed, and moving beds of catalyst.

The dehydration process may be operated as either a continuous or a batch process, preferably as a continuous process.

The dehydration process generates a crude reaction product comprising dimethyl ether and water as reaction products, unreacted methanol and one or more compounds selected from promoter compounds and promoter precursor compounds. One or more components of the crude reaction product may be recycled as feed to the process.

Dimethyl ether may be recovered from the crude reaction product by any suitable method, for example by distillation methods.

Without being bound by theory, the productivity of catalysts will typically decrease over time on stream; in industrially applied catalytic processes, one of the ways by which the decrease in productivity may be compensated for is by increasing the reaction temperature to maintain a consistent productivity. A disadvantage of increasing the temperature of the reaction is that this may lead to an increase in undesirable by-products or may result in a decrease in selectivity; another disadvantage of increasing the temperature of the reaction is that such an increase in temperature may accelerate the rate of catalyst deactivation. However, without wishing to be bound by theory, it is believed that in the present invention, decreases in productivity of the catalyst may be at least in part compensated for by increasing the relative concentration of the promoter in the methanol feed, and thus may reduce or eliminate the need for an increase in temperature to compensate for any reduction in productivity which may occur with time on stream; similarly, decreases in productivity of the catalyst may be at least in part compensated for by changing the promoter used or by adding a second or further additional promoter compound to the methanol feed as the time on stream increases.

In addition to the beneficial effect on the rate of dehydration of methanol reactions carried out in the presence of solid Brønsted acid catalysts which are aluminosilicate zeolites which have a 1-dimensional or 3-dimensional framework structure or heteropolyacids, it is believed that the use of promoters as described herein may result in an increase in the stability of the solid Brønsted acid catalyst and may make the solid Brønsted acid catalyst more resistant to deactivation by impurities present in the methanol feed.

In a further aspect of the present invention provides a process for dehydrating methanol to dimethyl ether product in the presence of a catalyst, wherein the catalyst is at least one solid Brønsted acid catalyst selected from (a) aluminosilicate zeolites which have a 1-dimensional or a 3-dimensional framework structure or (b) heteropolyacids, and wherein prior to using the catalyst in the dehydration process, the catalyst has been impregnated with a promoter selected from:

(i) at least one an alkyl carboxylate ester, $C_nH_{(2n+1)}CO_2CH_3$ (Formula I); or (ii) at least one di-ester compound, $C_mH_{2m}(CO_2CH_3)_2$ (Formula II), wherein in Formula I, n=1 to 11; and in Formula II, m=2 to 7.

In this further aspect of the invention, the feed to the dehydration process comprises methanol and may optionally comprise other components, for example dimethyl ether, water, or at least one compound which is a promoter compound of Formula I or Formula II or a precursor compound thereof.

The invention is now illustrated with reference to the following non-limiting Examples.

EXAMPLES

Details of the catalysts used in the Examples are provided in Table 1 below. In Table 1 only rings having 8 T atoms or greater are given. Smaller ring sizes have been omitted.

TABLE 1

| Catalyst | Framework Code | Framework Structure | Ring Size | SAR |
|---|---|---|---|---|
| Zeolite beta | BEA | 3-D | 12 | 25 |
| Zeolite Y | FAU | 3-D | 12 | 30 |
| Mordenite | MOR | 1-D | 12 | 20 |
| ZSM-22 | TON | 1-D | 10 | 69 |
| ZSM-5 | MFI | 3-D | 10 | 23 |
| SSZ-13 | CHA | 3-D | 8 | 24 |
| Ferrierite | FER | 2-D | 10.8 | 20 |
| Clinoptilolite | HEU | 2-D | 10.8 | 10 |
| SAPO-34 | CHA | 3-D | 8 | n/a |

SAR indicates the silica:alumina molar ratio of a zeolite
1-D, 2-D and 3-D indicate a 1-dimensional, 2-dimensional and 3-dimensional framework structure respectively
SAPO-34 is a silicoaluminophosphate
n/a means not applicable Examples 1 to 5

The methyl ester compounds used in Examples 1 to 5 were essentially pure compounds (a total organic nitrogen content of about 0.1 ppm, expressed as nitrogen on a ppm by weight basis) and were obtained from Sigma-Aldrich or Brenntag UK Limited.

The zeolites used in Examples 1 to 5 were utilised in their H-form. The zeolites Y and SAPO-34 were obtained in H-form from Zeolyst International. All other zeolites (except ZSM-22) were obtained in ammonium-form from Zeolyst International and converted to H-form by calcination in air at 500° C. H-ZSM-22 and silica-supported silicotungstic acid were prepared in accordance with the methods described below.

Preparation of H-ZSM-22

For use in the preparation of the zeolite the following solutions were prepared:

i) aluminium chlorohydrol solution (25.3 g aluminium chlorohydrol in 253 g of deionised water);

ii) potassium hydroxide solution (82 g 88.8% potassium hydroxide in 820 g of deionised water);

iii) Ludox solution (900 g Ludox AS40 (silica sol with 40 wt % $SiO_2$ stabilised with ammonium hydroxide ex Aldrich) diluted in 2694 g of deionised water);

iv) ammonium chloride (200.6 g ammonium chloride in 3750 g deionised water)

The aluminium chlorohydrol solution was added slowly with vigorous stirring to the potassium hydroxide solution of to form an aluminate solution. 226 g diaminohexane (DAH) was added to the aluminate solution. The DAH/aluminate solution was added to the Ludox solution under vigorous stirring and stirred for at least 30 minutes until a gel formed. The gel was transferred to an autoclave and agitated (500 rpm) at a temperature of 160° C. for 48 hours to form a slurry. The autoclave was allowed to cool, under agitation, to a temperature below 60° C. and the slurry centrifuged to separate the solids from the mother liquor. The solids were washed with sufficient deionised water such that the pH of was less than 8 and then dried overnight at a temperature of 110° C. to generate a dried zeolitic material. The X-ray diffraction pattern of the zeolitic material showed that the zeolite was ZSM-22. The dried zeolitic material was calcined at 600° C. for 12 hours to effect removal of the diaminohexane from the pores of the pores of the zeolite. The calcined zeolite was converted into the ammonium-form of the zeolite by ion-exchange with the ammonium chloride solution at a temperature of 80° C. for 4 hours and then repeated. The ion-exchanged zeolite was separated from the liquid by filtration, washed with deionised water and dried overnight at 110° C. The ammonium-exchanged zeolite was converted to the H-form by calcination in air at 500° C. for 8 hours.

Preparation of Silica-Supported Silicotungstic Acid Catalyst 30.1 g silica (ex Grace Chemicals) was added to a solution of 14.30 g silicotungstic acid (ex Nippon Organic Chemicals) in 39.9 g water. The silica/silicotungstic acid solution was left to stand for 30 minutes before being oven dried at a temperature of 120° C. for a period of 16 hours. The dried catalyst material was then cooled to 50° C. 40.93 g catalyst was obtained which contained 19.5 wt % of tungsten.

The methanol dehydration reactions of Examples 1 to 5 were carried out utilising the General Reaction Method and Apparatus described below.

General Reaction Method and Apparatus

The methanol dehydration reactions were carried out using a 16-channel parallel fixed-bed stainless steel reactor system. Each reactor (2 mm internal diameter) was heated to maintain a temperature of 150° C. Each reactor housed a 25 mg bed of catalyst (having particle size fraction of 100 to 200 microns diameter) loaded on top of a 6 cm deep bed of an inert material (carborundum). The reactor volume above the catalyst was also packed with carborundum.

Each reactor was maintained at a temperature of 150° C. and at a total pressure of 1100 kPa throughout the reactions. A gaseous feed comprising 10 mol % methanol and inert gas was introduced into the reactor and allowed to flow through the catalyst bed for a period of 48 hours at which point a promoter compound was added to the feed to achieve a gaseous feed comprising 10 mol % methanol and 5 mol % promoter compound (relative to methanol). This gaseous feed comprising the promoter compound was introduced into the reactor for a period of 24 hours at a constant flow rate of methanol of 13 mmol h$^{-1}$ and a constant promoter flow rate of 0.7 mmol h$^{-1}$.

The effluent stream from each reactor was diluted with inert gas (nitrogen) and was periodically analysed by online gas chromatography to determine the yield of dimethyl ether product.

Example 1

This Example demonstrates the effect of various alkyl carboxylate ester promoter compounds on the dehydration of methanol employing a variety of catalysts.

Methanol dehydration reactions were carried out in accordance with the General Reaction Method and Apparatus described above using the alkyl carboxylate ester compounds and catalysts specified in Table 2 below. The observed space time yields to dimethyl ether product are also provided in Table 2.

TABLE 2

| | Dimethyl ether STY/g kg$^{-1}$ h$^{-1}$ for different promoters | | | | | | | |
|---|---|---|---|---|---|---|---|---|
| Catalyst | None | methyl acetate | methyl propionate | methyl n-butyrate | methyl n-pentanoate | methyl n-hexanoate | methyl n-heptanoate | methyl n-octanoate |
| zeolite beta | 209 | 568 | — | — | 837 | 993 | 975 | 1045 |
| ZSM-22 | 331 | 346 | 392 | 455 | 533 | 685 | 787 | 851 |
| mordenite | 885 | 1450 | 1615 | 1773 | 2221 | 2459 | 2399 | 2497 |
| ZSM-5 | 862 | 1255 | 1391 | 1663 | 1999 | 2053 | 1863 | 1890 |
| zeolite Y | 36 | 59 | 67 | 84 | 119 | 135 | 150 | 153 |
| SSZ-13 | 1402 | — | — | 1766 | 1827 | 1809 | 1647 | 1662 |
| ferrierite | 2568 | 2460 | 2518 | 2534 | 2689 | 2613 | 2555 | 2571 |
| clinoptilolite | 1285 | — | — | — | — | 1292 | 1267 | 1242 |
| SAPO-34 | 1155 | — | — | — | 819 | 763 | 715 | 792 |
| STA | 1359 | — | — | — | 1611 | 1506 | 1481 | 1478 |

As Table 2 shows, in the presence of the alkyl carboxylate ester compounds the productivities to dimethyl ether increased where a 1-dimensional or a 3-dimensional aluminosilicate zeolite or a heteropolyacid catalyst was used in the reactions. However, and taking into account experimental error, no increase in dimethyl ether productivity was observed where a 2-dimensional zeolite (ferrierite and clinoptilolite) or a silicoaluminophosphate (SAPO-34) was used as the catalyst.

Example 2

This Example demonstrates the effect of straight chain and branched chain alkyl carboxylate ester compounds on the catalytic dehydration of methanol.

Methanol dehydration reactions were carried out in accordance with the General Reaction Method and Apparatus described above in the presence of the catalysts and promoter compounds specified in Table 3 below. The observed space time yields to dimethyl ether product are provided in Table 3.

TABLE 3

| Catalyst | Dimethyl ether STY/g kg$^{-1}$ h$^{-1}$ | | |
|---|---|---|---|
| | No promoter | Methyl n-butyrate | Methyl iso-butyrate |
| ZSM-5 | 841 | 1663 | 941 |
| mordenite | 835 | 1773 | 1182 |
| ZSM-22 | 313 | 455 | 371 |
| zeolite Y | 35 | 84 | 58 |
| ferrierite | 2476 | 2534 | 2429 |

As the results in Table 3 show, the addition of the straight chain and branched chain alkyl carboxylate ester compounds provided increased productivity to dimethyl ether in those reactions carried out using 1-dimensional or 3-dimensional zeolite catalysts. In contrast, no improvement in productivity was observed in the experiments which used a 2-dimensional zeolite catalyst (ferrierite).

Example 3

This Example demonstrates the effect of different concentrations of methyl n-butyrate on the catalytic dehydration of methanol.

Methanol dehydration reactions were carried out in accordance with the General Reaction Method and Apparatus described above utilising the catalysts and promoter concentrations as specified in Table 4 below. The various promoter concentrations (relative to methanol) were achieved by adjusting the the flow rate of promoter to be in the range 0.27 mmol h$^{-1}$ to 2.7 mmol h$^{-1}$ depending on the desired promoter concentration to be achieved. The observed space time yields to dimethyl ether product are provided in Table 4.

TABLE 4

| Relative promoter concentration | Dimethyl ether STY/g kg$^{-1}$ h$^{-1}$ | | | |
|---|---|---|---|---|
| (mol %) | Ferrierite | SSZ-13 | ZSM-5 | ZSM-22 |
| 0 | 2610 | 1404 | 831 | 338 |
| 2 | 2608 | 1653 | 1288 | 420 |
| 5 | 2646 | 1766 | 1567 | 449 |
| 10 | 2625 | 1803 | 1694 | 538 |
| 15 | 2624 | 1831 | 1738 | 587 |
| 20 | 2598 | 1821 | 1723 | 630 |

As the results in Table 4 show, in those reactions which employed either a 1-dimensional or a 3-dimensional zeolite as the catalyst, the productivities to dimethyl ether increased at all promoter concentrations. However, and within experimental error, where the catalyst was a 2-dimensional zeolite (ferrierite), essentially no improvement in dimethyl ether productivity was observed at any level of promoter concentration.

Example 4

This Example demonstrates the effect of various alkyl carboxylate ester compounds on the catalytic dehydration of methanol in the presence of the zeolite ZSM-5 at various silica:alumina molar ratios (SAR). The methanol dehydration reactions were carried out in accordance with the General Reaction Method and Apparatus described above using the promoter compounds identified in Table 5 below. The observed space time yields to dimethyl ether product are provided in Table 5.

TABLE 5

| Promoter | Dimethyl ether STY/g kg$^{-1}$ h$^{-1}$ | | |
|---|---|---|---|
| | ZSM-5 SAR 23 | ZSM-5 SAR 80 | ZSM-5 SAR 280 |
| no promoter | 862 | 377 | 92 |
| methyl acetate | 1255 | 949 | 264 |
| methyl propionate | 1391 | 1166 | 320 |
| methyl n-butyrate | 1663 | 1564 | 399 |
| methyl iso-butyrate | 941 | 701 | 177 |
| methyl n-pentanoate | 1999 | 2332 | 646 |
| methyl n-hexanaoate | 2053 | 2648 | 998 |
| methyl n-heptanoate | 1863 | 2470 | 897 |
| methyl n-octanoate | 1890 | 2274 | 889 |

As can be seen from an inspection of Table 5, the use of the straight and branched chain alkyl carboxylate ester compounds enabled an increase in dimethyl ether productivity to be achieved in reactions utilising zeolite catalysts of different silica:alumina molar ratios.

Example 5

This Example demonstrates the effect of different concentrations of various alkyl carboxylate ester and di-ester compounds on the catalytic dehydration of methanol in the presence of the zeolite mordenite and the zeolite ZSM-5 with a silica:alumina molar ratio (SAR) of 20 and 80, respectively.

Methanol dehydration reactions were carried out in accordance with the General Reaction Method and Apparatus described above using the alkyl carboxylate ester and diester compounds and concentration as specified in Tables 6 and 7 below. The various promoter concentrations (relative to methanol) were achieved by adjusting the the flow rate of promoter to be in the range 0.0013 mmol h$^{-1}$ to 0.013 mmol h$^{-1}$ depending on the desired promoter concentration to be achieved. The observed space time yields to dimethyl ether product are provided in Tables 6 and 7 for the zeolite mordenite and zeolite ZSM-5 catalysts, respectively.

TABLE 6

ZSM-5 SAR 80

| Co-feed | Dimethyl ether STY/g kg$^{-1}$ h$^{-1}$ for different co-feed concentrations | | |
|---|---|---|---|
| | 0 mol % | 0.01 mol % | 0.1 mol % |
| methyl n-hexanoate | 387 | 516 | 1123 |
| methyl n-nonanoate | 418 | 979 | 1396 |
| dimethyl succinate | 382 | 774 | 1487 |
| dimethyl glutarate | 371 | 1345 | 2177 |

TABLE 7

Mordenite SAR 20

Dimethyl ether STY/g kg$^{-1}$ h$^{-1}$ for different co-feed concentrations

| Co-feed | 0 mol % | 0.01 mol % | 0.1 mol % |
|---|---|---|---|
| methyl n-hexanoate | 835 | 880 | 1053 |
| methyl n-nonanoate | 926 | 1159 | 1663 |
| dimethyl succinate | 912 | 1134 | 1797 |
| dimethyl glutarate | 936 | 1485 | 2349 |

As the results in Tables 6 and 7 show, in the presence of the alkyl carboxylate ester compounds the productivities to dimethyl ether increased at all promoter concentrations tested.

Example 6

This Example demonstrates the effect of different concentrations of di-ester on the catalytic dehydration of methanol in the presence of the zeolite mordenite and the zeolite ZSM-5 with a silica:alumina molar ratio (SAR) of 20 and 80, respectively. Methanol dehydration reactions were carried out in accordance with the General Reaction Method and Apparatus described above using dimethyl adipate and concentration as specified in Tables 8 and 9 below. The various promoter concentrations (relative to methanol) were achieved by adjusting the the flow rate of promoter to be in the range 0.00013 mmol h$^{-1}$ to 0.013 mmol h$^{-1}$ depending on the desired promoter concentration to be achieved. The observed space time yields to dimethyl ether product are provided in Tables 8 and 9 for the zeolite mordenite and zeolite ZSM-5 catalysts, respectively.

TABLE 8

ZSM-5 SAR 80

Dimethyl ether STY/g kg$^{-1}$ h$^{-1}$ for different co-feed concentrations

| | 0 mol % | 0.001 mol % | 0.01 mol % | 0.1 mol % |
|---|---|---|---|---|
| dimethyl adipate | 390 | 652 | 1430 | 2265 |

TABLE 9

Mordenite SAR 20

Dimethyl ether STY/g kg$^{-1}$ h$^{-1}$ for different co-feed concentrations

| | 0 mol % | 0.001 mol % | 0.01 mol % | 0.1 mol % |
|---|---|---|---|---|
| dimethyl adipate | 817 | 965 | 1327 | 2030 |

As the results in Tables 8 and 9 show, the productivities to dimethyl ether increased at all promoter concentrations tested.

Example 7

This Example demonstrates the effect of dimethyl adipate on the catalytic dehydration of methanol in the presence of various zeolite and heteropolyacid catalysts.

The methanol dehydration reactions were carried out using the H-form of the zeolites and the heteropolyacids specified in Table 10 below.

Zeolite Y was obtained in H-form from Zeolyst International. Ferrierite, ZSM-22, ZSM-5, zeolite beta and mordenite were obtained in ammonium form from Zeolyst International and converted to H-form by calcination in air at 500° C. The silicoaluminophosphate SAPO-34 can be prepared using known literature methods or can be purchased commercially.

Dimethyl adipate was obtained from ACROS ORGANICS.

The silicotungstic acid used in the dehydration reactions was supported on silica and prepared in accordance with the method described below.

512 g silica (ex Evonik) was added to a solution of 508 g silicotungstic acid (ex Nippon Organic Chemicals) in 1249 g water to form a silica/silicotungstic acid solution which was left to stand for 30 minutes. Excess silicotungstic acid solution was removed by filtration and the resultant solid catalyst material was oven dried at a temperature of 110° C.

The dried catalyst was cooled to a temperature of 50° C. 685 g of catalyst was obtained which contained 18.9 wt % of tungsten.

The dehydration reactions for this Example 6 were carried out as follows, using a 16-channel parallel fixed-bed stainless steel reactor system. Each reactor (10 mm internal diameter) housed a catalyst bed of 0.168 g catalyst diluted with 0.337 g silica. The particle sizes of the catalyst and silica were in the range 450 to 900 microns in diameter. The catalyst mixture was loaded on top of a 6.5 cm deep bed of an inert material (quartz sand). The reactor volume above the catalyst bed was also packed with quartz sand.

Each reactor was maintained at a temperature of 150° C. and at a total pressure of 1100 kPa throughout the dehydration reactions. A gaseous feed comprising 10 mol % methanol and inert gas was introduced into the reactor and allowed to flow through the catalyst bed for a period of 48 hours at which point a promoter compound was added to the feed to achieve a gaseous feed comprising 10 mol % methanol and 5 mol % promoter compound (relative to methanol). This gaseous feed comprising the promoter compound was introduced into the reactor for a period of 24 hours at a constant flow rate of methanol of 45 mmol h$^{-1}$ and a constant promoter flow rate of 2.3 mmol h$^{-1}$.

The effluent stream from each reactor was cooled to 5° C. in a condenser and the gas phase from the condenser was periodically analysed by online gas chromatography to determine the yield of dimethyl ether product. The observed space time yields to dimethyl ether product are given in Table 8 below.

TABLE 10

| | | Dimethyl ether STY/g kg$^{-1}$ h$^{-1}$ | |
|---|---|---|---|
| Catalyst | Structure | No Promoter | Dimethyl adipate |
| ZSM-22 | 1-D | 375 | 593 |
| ZSM-5 SAR23 | 3-D | 586 | 1636 |
| ZSM-5 SAR50 | 3-D | 312 | 1432 |
| ZSM-5 SAR280 | 3-D | 93 | 593 |
| zeolite Y | 3-D | 55 | 205 |
| zeolite beta | 3-D | 156 | 866 |

TABLE 10-continued

| | | Dimethyl ether STY/g kg$^{-1}$ h$^{-1}$ | |
|---|---|---|---|
| Catalyst | Structure | No Promoter | Dimethyl adipate |
| mordenite | 1-D | 620 | 1912 |
| STA/silica | n/a | 402 | 1477 |
| ferrierite | 2-D | 1558 | 1227 |
| SAPO-34 | 3-D | 637 | 167 |

SAR indicates the silica:alumina molar ratio of the ZSM-5 zeolite
1-D, 2-D and 3-D indicate a 1-dimensional, a 2-dimensional and a 3-dimensional framework structure respectively.
n/a means not applicable.

As can be seen from an inspection of Table 10, in the presence of the di-ester compound, the space time yields to dimethyl ether were seen to increase in the case of the 1-dimensional and 3-dimensional aluminosilicate zeolites and heteropolyacid catalysts. However, in the case of the 2-dimensional and non-aluminosilicate zeolite catalyst (SAPO-34), the addition of the di-ester compound was found to inhibit the space time yields to dimethyl ether.

Example 8

Preparation of H-ZSM-5

Zeolite ZSM-5 in the ammonium form (ex. Zeolyst International) was converted to H-form by calcination in air at 500° C.

Preparation of Dimethyl Adipate Impregnated H-ZSM-5

A 1.5196 g sample of the H-form zeolite prepared as described above was added to a solution of 0.0891 g of dimethyl adipate in 10 ml deionised water. The mixture stirred at room temperature for 10 minutes and then concentrated in vacuo before being dried in an oven at 110° C. for 24 h.

Reaction Testing

Samples of the H-ZSM-5 and the dimethyl adipate impregnated H-ZSM-5 were pressed and sieved to a particle size fraction of 100 to 200 microns diameter and The methanol dehydration reactions of Example 8 were carried out utilising the General Reaction Method and Apparatus described above without the addition of a promoter compound to the gaseous feed. The observed space time yields to dimethyl ether product are provided in Table 11 below.

TABLE 11

| | DME STY/g kg$^{-1}$ h$^{-1}$ | |
|---|---|---|
| Catalyst | ~3 hours after introduction of MeOH feed | ~12 hours after introduction of MeOH feed |
| H-ZSM-5 SAR 80 | 409 | 385 |
| H-ZSM-5 SAR 80 impregnated with dimethyl adipate | 1009 | 543 |

The invention claimed is:

1. A process comprising dehydrating methanol to dimethyl ether product in the presence of a catalyst and a promoter,
wherein the catalyst is at least one solid Brønsted acid catalyst selected from (a) aluminosilicate zeolites which have a 1-dimensional or a 3-dimensional framework structure, and (b) heteropolyacids, and
wherein the promoter is:
(i) at least one an alkyl carboxylate ester, $C_nH_{(2n+1)}CO_2CH_3$ (Formula I); or
(ii) at least one di-ester compound, $C_mH_{2m}(CO_2CH_3)_2$ (Formula II),
wherein in Formula I, n is 2 to 11; and in Formula II, m is 2 to 7 and wherein the molar ratio of promoter to methanol is maintained at less than 1.

2. A process according to claim 1 wherein the alkyl carboxylate ester of Formula I is a straight chain alkyl carboxylate ester.

3. A process according to claim 1 wherein in Formula I, n is 2 to 9.

4. A process according to claim 1 wherein in Formula I, n is 3 to 7.

5. A process according to claim 1 wherein the total amount of promoter relative to methanol is maintained in an amount of at least 1 ppm.

6. A process according to claim 1 wherein the molar ratio of promoter to methanol is maintained in the range 0.00001:1 to 0.2:1.

7. A process according claim 1 wherein the promoter is added to the dehydration process.

8. A process according to claim 1 wherein the promoter is generated in-situ in the dehydration process.

9. A process according to claim 1 in which process the feed components to the process are methanol, one or both of (i) at least one promoter compound of Formula I or Formula II and (ii) at least one precursor compound of a promoter compound of Formula I or Formula II; and one or both of dimethyl ether and water.

10. A process according to claim 1 wherein the Brønsted acid catalyst is a zeolite which zeolite is a H-form zeolite.

11. A process according to claim 1 wherein the Brønsted acid catalyst is a zeolite having a 1-dimensional framework structure selected from framework types MOR, MTT and TON.

12. A process according to claim 1 wherein the Brønsted acid catalyst is a zeolite having a 3-dimensional framework structure selected from framework types MFI, FAU, CHA and BEA.

13. A process according to claim 1 wherein the Brønsted acid catalyst is a zeolite which zeolite is a medium or large pore zeolite.

14. A process according to claim 1 wherein the Brønsted acid catalyst is a zeolite which zeolite is composited with a binder material.

15. A process according to claim 1 wherein the Brønsted acid catalyst is a heteropolyacid which heteropolyacid is a silicotungstic acid.

16. A process according to claim 1 wherein the process is carried out at a temperature of from 100° C. to 300° C.

17. A process according to claim 1 wherein the process is carried out as a heterogeneous vapour phase process.

18. A method of improving the productivity to dimethyl ether product in a process for dehydrating methanol in the presence of a catalyst and a promoter,
wherein the catalyst is at least one solid Brønsted acid catalyst selected from (a) aluminosilicate zeolites which have a 1-dimensional or a 3-dimensional framework structure, and (b) heteropolyacids, and
wherein the promoter is:
(i) at least one an alkyl carboxylate ester, $C_nH_{(2n+1)}CO_2CH_3$ (Formula I); or
(ii) at least one di-ester compound, $C_mH_{2m}(CO_2CH_3)_2$ (Formula II), wherein in Formula I, n is 2 to 11; and in Formula II, m is 2 to 7 and wherein the molar ratio of promoter to methanol is maintained at less than 1.

\* \* \* \* \*